United States Patent [19]

Thramann

[11] Patent Number: 5,360,448
[45] Date of Patent: Nov. 1, 1994

[54] POROUS-COATED BONE SCREW FOR SECURING PROSTHESIS

[76] Inventor: Jeffrey J. Thramann, 420 E. 70th St., New York, N.Y. 10021

[21] Appl. No.: 6,653

[22] Filed: Jan. 19, 1993

Related U.S. Application Data

[63] Continuation-in-part of Ser. No. 772,284, Oct. 7, 1991, abandoned.

[51] Int. Cl.⁵ .............................................. A61F 8/28
[52] U.S. Cl. .................................. 623/16; 606/73; 606/76; 411/424; 411/900; 623/18
[58] Field of Search ............................. 623/16–18; 606/73, 76; 411/424, 900, 385

[56] References Cited

U.S. PATENT DOCUMENTS

| | | | |
|---|---|---|---|
| 471,179 | 3/1892 | Jones | 411/424 |
| 3,852,045 | 12/1974 | Wheeler et al. | 606/76 X |
| 3,905,777 | 9/1975 | Lacroix | 606/76 X |
| 4,052,754 | 10/1977 | Homsy | 623/16 X |
| 4,177,524 | 12/1979 | Grell et al. | 606/73 X |
| 4,259,072 | 3/1981 | Hirabayashi et al. | 623/16 X |
| 4,599,085 | 7/1986 | Riess et al. | 623/16 |
| 4,632,100 | 12/1986 | Somers et al. | 606/73 |
| 4,883,491 | 11/1989 | Mallory et al. | |
| 5,019,079 | 5/1991 | Ross | 606/72 |
| 5,084,050 | 1/1992 | Draenert | 606/77 |
| 5,094,618 | 3/1992 | Sullivan | 623/16 X |
| 5,098,434 | 3/1992 | Serbousek | 606/73 |
| 5,152,795 | 10/1992 | Sioshansi et al. | 623/16 |

FOREIGN PATENT DOCUMENTS

| | | | |
|---|---|---|---|
| 0176711 | 4/1986 | European Pat. Off. | |
| 0475358 | 3/1992 | European Pat. Off. | 623/18 |
| 2610512 | 8/1988 | France | 623/16 |
| 1961531 | 7/1970 | Germany | 623/16 |
| 2628443 | 12/1976 | Germany | 623/18 |
| 0840759 | 7/1960 | United Kingdom | 411/424 |
| 2220571 | 12/1990 | United Kingdom | 623/16 |

*Primary Examiner*—David H. Willse
*Attorney, Agent, or Firm*—Brooks Haidt Haffner & Delahunty

[57] ABSTRACT

Bone screws are disclosed with and without heads and with the screw shaft provided with axially adjacent longitudinally extending regions, one or more of which have bone ingrowth porous surfaces and alternate with regions having threaded surfaces. The headed embodiments have a region with a threaded surface nearest the head.

7 Claims, 2 Drawing Sheets

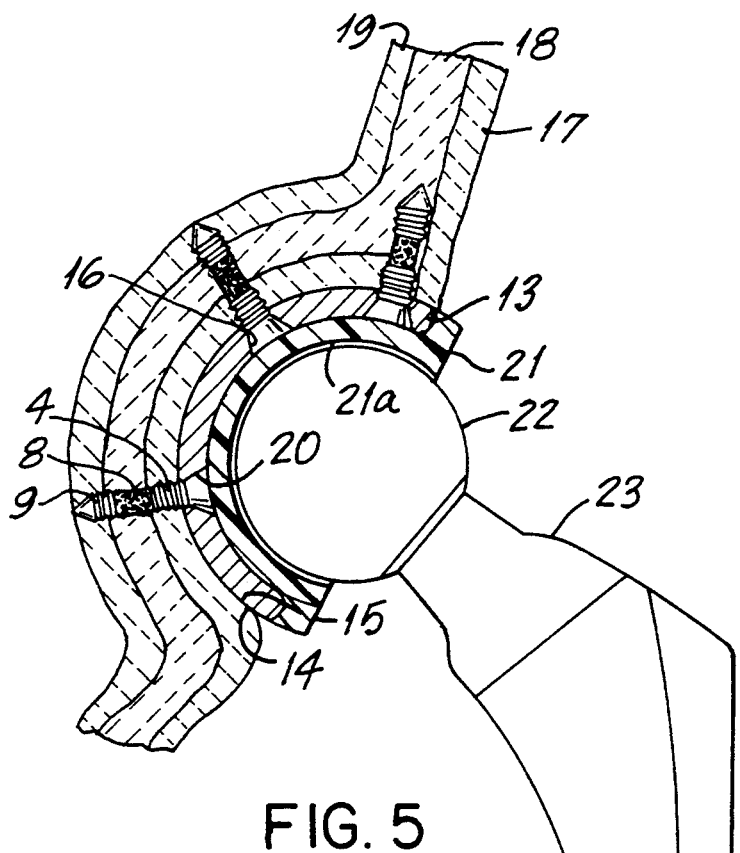
FIG. 5
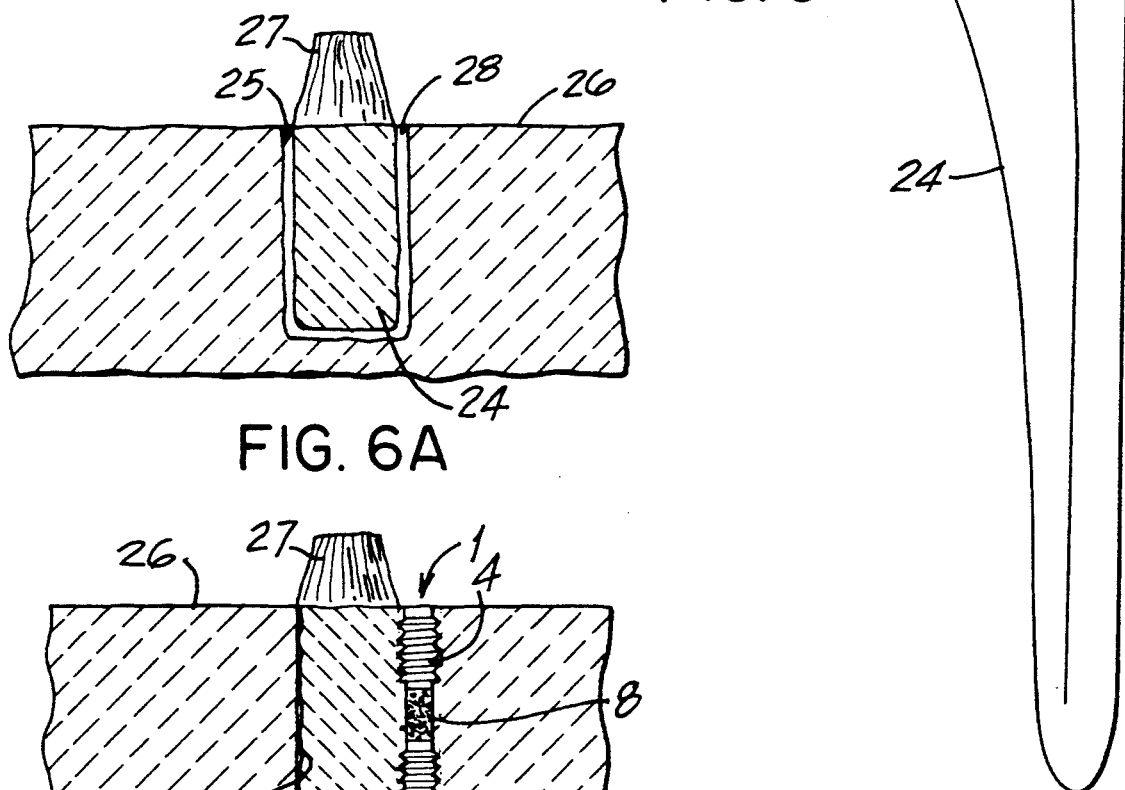
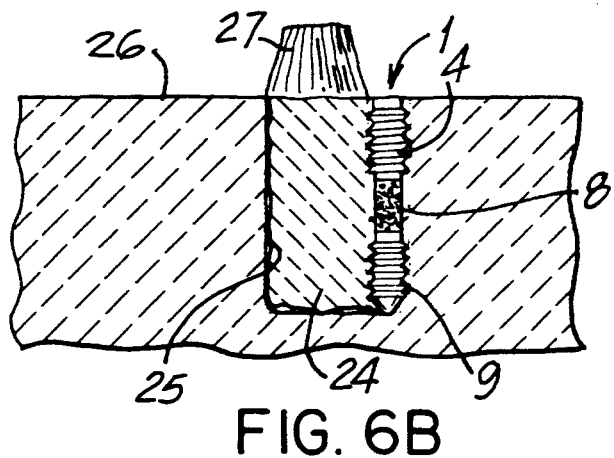
FIG. 6A
FIG. 6B

POROUS-COATED BONE SCREW FOR SECURING PROSTHESIS

CROSS REFERENCE TO RELATED APPLICATION

This application is a continuation-in-part of my U.S. application Ser. No. 07/772,284, filed Oct. 7, 1991 now abandoned, entitled "Screw For Securing Acetabular Prosthesis In Cementless Applications."

BACKGROUND OF THE INVENTION

This invention relates to bone screws used in the fixation of artificial prosthesis or autogenous grafts within the body and, in particular, to the short and long-term mechanical fixation of such components in their application to joint reconstruction. More specifically, the invention is directed to a screw for securing an acetabular cup of an acetabular prosthesis or for a bone-tendon autograft in an anterior cruciate ligament (ACL) repair procedure.

One of the critical problems with the use of artificial joints to replace diseased or traumatized joints is acquiring a reliable attachment of the prosthesis to the bone in order to achieve both initial and long-term fixation. The most widely used method to secure a prosthesis to bone and provide fixation involves the use of bone cement. While this approach in general provides a strong initial bond, it has been found that the bone cement process is inadequate and undesirable since, through a multitude of possible mechanisms upon which no consensus has been reached, the bone-cement interface eventually breaks down. In situ, the cement is often the first part of the prosthetic reconstruction to fail during use.

Current attempts to increase prosthesis function have focused on establishing long-term fixation between the implant and the surrounding bone. The technology that has been developed to meet this need involves the provision of prosthetic implants with porous-coated areas designed to accept bone ingrowth. It has been found that in order to optimize the potential of this porous-coated technology, it is imperative to maximize the porous-coated area of the prosthesis in contact with the adjacent bone. However, a substantial number of implants continue to fail over time. Lack of significant bone ingrowth is a leading cause of such failures and this has been attributed in part to inadequate initial fixation and micromotion between the implant and the bone.

Numerous attempts to improve initial fixation and prevent micromotion have been developed. For instance, U.S. Pat. No. 4,883,491 discusses the use of an acetabular cup with an outer surface which includes screw threads. The screw threads provide for the cup to be attached directly into the acetabular socket through the application of torque to the cup at the time of implantation. This is disclosed as providing strong initial fixation of the implant to the bone. To provide long-term fixation to the bone, the acetabular cup disclosed in U.S. Pat. No. 4,883,491 includes porous-coated columns in an alternating pattern with the screw threads on the surface of the cup. One drawback of such an implant is that its installation requires removal of significant amounts of subchondral bone. Recent studies have shown that removal of large amounts of subchondral bone results in loss of the subchondral plate, weakening of the pelvis and inadequate long-term fixation.

Others have attempted to provide initial and long-term fixation through the combination of a porous-coating on the implant, and bone screws to provide for initial fixation. Current screws used to secure a cementless acetabular prosthesis in total hip replacements consist of a simple spiral shank screw. The screw is intended to provide initial stability to the implant, while long-term stability is dependent both on the initial stability of the screws and subsequent bone ingrowth into the porous-coated area on the external surface of the acetabular cup.

Currently, upwards of 40% of all acetabular implants fail at ten years, with the incidence of failure increasing substantially thereafter. Even with recent advances, it has been noted that the primary reason for failure is loosening of the acetabular implant. While the cementless implant has sufficient initial stability through support from the screws, the screws cannot maintain the stability required to effectively initiate bone ingrowth since they provide no mechanism for increasing stability once inserted into the pelvis. As a result, the stresses that are continually transferred to the screws act to slowly work the screws loose and subsequently decrease implant support. The increasing ineffectiveness of the screws then transfers more stress to the acetabular cup itself, which results in micromotion of the prosthesis followed by the accumulation of prosthetic wear debris and an inflammatory immune reaction that destroys the bone-implant boundary. The result is concluded to be complete prosthetic failure.

Acetabular cups used in conjunction with screws are often provided with porous-coated fixation pegs and fins. Although these devices provide good initial mechanical fixation, many problems remain. For instance, acetabular prostheses that have been designed to date have failed to prevent the main mode of acetabular failure, where the acetabular prosthesis sinks into the bony pelvis. In addition, no attempt has been made to maintain the initial fixation provided by the bone screw or threaded acetabular cup for the purpose of long-term fixation. Thus, while threaded acetabular cups, and acetabular cups secured by bone screws, provide strong initial fixation, the literature has shown that resorption occurs around the screw threads after six to eight weeks. As a result, the screws are rendered less effective after this period of time and some of the stress initially carried by these screws or acetabular threads is transferred to the prosthesis.

The continuous transfer of stresses to the prosthetic implant alters the stress shielding characteristics of the implant, and creates a progressive syndrome of stress shielding. This syndrome results in a continuously changing pattern of bone resorption and hypertrophy, leading to instability of the implant. In addition, the continually changing pattern of resorption and hypertrophy, as well as the transfer of stresses to the prosthesis, results in micromotion of the whole assembly.

Reconstruction of the hip joint with an artificial prosthesis is not the only surgical reconstructive procedure plagued with problems of long-term viability. Anterior cruciate ligament repair procedures have utilized numerous techniques ranging from extraosseosis fixation of the autologous bone-tendon graft with screws and staples to the use of completely artificial ligaments in an attempt to provide increased long-term viability of the reconstructed joint (knee). Because problems with artificial ligament development have not yet been adequately worked out, and for a multitude of other reasons based on surgical preference, arthroscopic compatability and such, bone tendon autografts using patellar tendons have become the graft of choice for anterior cruciate ligament reconstruction.

Secure immediate and long-term fixation of the graft is critical to the success of the procedure. This will be better understood with an understanding of the basic method in which ACL repair procedures are performed. A bone plug is taken from both the patella and the tibial tuberosity which are connected to each other by the patellar ligament. A bone-tendon autograft involves securing a patellar bone plug, patellar ligament and tibial bone plug. To perform the ACL procedure, two holes are drilled, one in the distal femur and one in the proximal tibia. The bone-tendon autograft is then inserted into the holes such that the tibial bone plug is in the tibial hole and the patellar bone plug is in the femoral hole. The patellar ligament thus assumes a position similar to the natural position of the ACL.

The bone plugs are commonly secured within their holes by an interference fit with a Kurosaka screw. Optimally, the Kurosaka screw maintains adequate fixation of the graft such that bone plug to bone fixation can secure the graft permanently. However, problems have arisen with this procedure in that resorption around the Kurosaka screw and the potential for stress shielding and subsequent bone remodeling cause a progressive slipping of the screw in the face of the constant pulling force of the tendon against the screw. Eventually the tendon becomes sufficiently lax to cause complete failure of the reconstruction.

SUMMARY OF THE PRESENT INVENTION

In view of the foregoing state of the art, it is an object of the present invention to provide an improved bone screw which increases the fixation of both prosthetic implants and bone-tendon autografts, thus providing for longer successful fixation and reconstruction as compared to current procedures. More particularly, it is an object of the present invention to provide long term stability through fixation of the screw to the bone, resulting in long-term viability of the prosthetic and autograft reconstruction.

It is another object of the invention to minimize the progression of stress shielding by maintaining continual fixation of the screws throughout the life of the reconstruction and thus reducing the transfer of stress from the screws to the acetabular prosthesis or bone-tendon autograft. It is a further object of the invention to provide improved long-term resistance to both shear stresses and inward forces which tend to push the acetabular implant into the bony pelvis resulting in the most common mechanism of acetabular prosthesis failure. It is also an object of the invention to provide improved long-term resistance to both shear stresses and outward forces which tend to pull a bone-tendon autograft out of the bony femor or tibia.

It is a further object of the invention to provide improved initial and long-term fixation of the acetabular implant, without requiring the complex manufacture and implantation of an acetabular cup with a threaded and porous-coated outer surface, and to minimize the amount of subchondral bone that must be removed from the acetabular socket for installation of an acetabular cup.

To achieve the foregoing objects, the present invention provides a bone screw including a shaft having an outer surface including a screw thread section for engagement with bone, and a porous-coated section which allows for bone ingrowth into or through that portion of the surface of the screw shaft.

In one preferred embodiment, the shaft surface includes at least two distinct and end to end axially related sections. A first section on the shaft surface is adjacent a screw head and has a threaded surface for secure initial attachment of the bone screw to bone, and a second section on the shaft surface is adjacent the first section but separated from the screw head by the first section, the second section having a porous-coated ingrowth material on its surface for long-term fixation of the bone screw to the bone.

In another preferred embodiment, the shaft surface includes a third section adjacent the second section but separated from both the first section and the screw head by the second section, the third section having a threaded surface.

In yet another embodiment, the shaft surface includes three sections as in the above embodiment, but the first and third sections have porous-coated ingrowth material on their surfaces for long-term fixation of the bone screw to the bone, and the second section has a threaded surface for secure initial attachment of the bone screw to the bone.

BRIEF DESCRIPTION OF THE DRAWINGS

The invention will be better understood after reading the following detailed description of the presently preferred embodiments with reference to the appended drawings in which:

FIG. 5 is a side elevation view, partially in section, of a screw/acetabular cup/hip stem prosthesis; and FIGS. 6A and 6B are cross-sectional views showing the use of a screw of the present invention in a bone-tendon autograft.

The same reference numerals are used throughout the drawings to designate the same or similar parts.

DESCRIPTION OF THE PRESENTLY PREFERRED EMBODIMENTS

Figure 1:
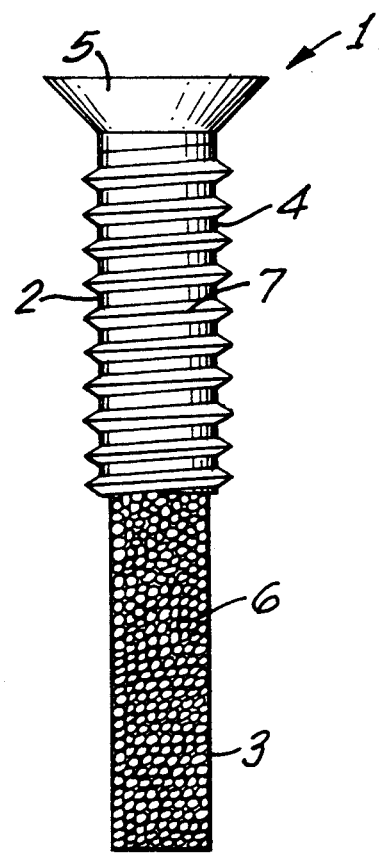
FIG. 1 is a side elevation view of a threaded screw constructed in accordance with the present invention.

Referring to the drawings, there is shown in FIG. 1 a preferred embodiment of a bone screw 1 of the present invention having a shaft 2 with a head 5 at one end and two distinct and axially adjacent longitudinally extending regions, a bone ingrowth region 3 and a threaded region 4 provided with threads 7. The threaded region 3 is adjacent or proximal to the head 5. The shaft 2 comprises a metal core integral with the head 5. The bone ingrowth region 3 is provided by a coating of a porous bone ingrowth material 6 on the core of shaft 2. The porous-coated section 3 provides for permanent fixation of the screw to the bone and the screw thread 7 of proximal section 4 provides initial fixation of the screw in cortical bone.

As clearly shown in FIG. 1, the thread 7 is of larger diameter than the porous section 3. In the use of the screw shown in FIG. 1 with acetabular cups, the screw of FIG. 1 is installed in a manner similar to conventional screws. Preferably a precisely drilled hole substantially equal in diameter to the outer diameter of the porous section 3 is provided in the bone, bored to a depth equal to the length of the shaft 2, so as to maximize bone to porous-coated ingrowth material 6 contact. After the hole is bored, the screw is inserted into the precision hole and screwed into place. The porous-coated section 3 enters the bored hole with a close interference fit, and the screw thread 7, having a greater diameter than the bored hole, engages the sides of the upper portion of the hole, engaging cortical bone for initial fixation of the bone screw, thereby anchoring the acetabular prosthesis. Since bone formation around screws is active for approximately six to eight weeks, the threaded (proximal) region or section 4 of the screw stabilizes the bone screw or the prosthesis during this time. During this period, the porous-coated distal region or portion 3 accommodates bone ingrowth to ultimately provide for long-term fixation of the screw and implant. During bone ingrowth, stresses originally carried by the threaded section 4 of the screw are gradually shared with porous-coated section 3, resulting in a reduced stress load carried by the threaded section 4. As a result, the impact of bone resorption in the area of the threaded section 4 of the screw is minimized, since the porous-coated section 3 takes over the stress burden throughout the remaining life of the implant. Stress transfer to the acetabular prosthesis is thus minimized, resulting in a reduction in the majority of bone remodeling around the prosthesis and yielding more reliable and stable long-term fixation.

Figure 2:
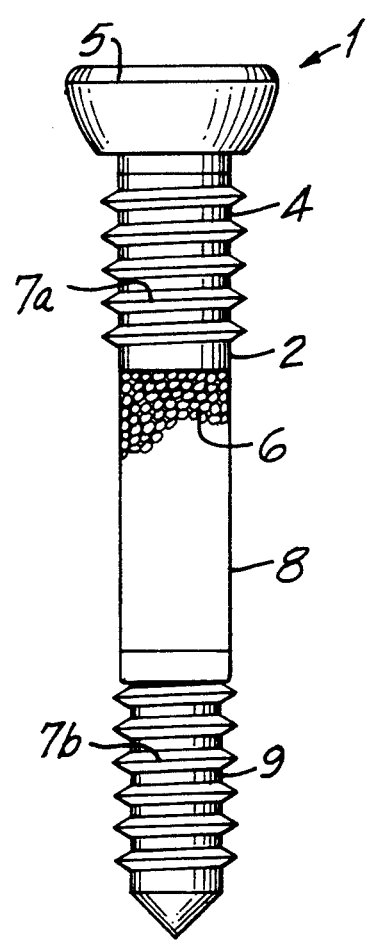
FIG. 2 is a side elevation view of another embodiment of a threaded screw constructed in accordance with the present invention.
Figure 3:
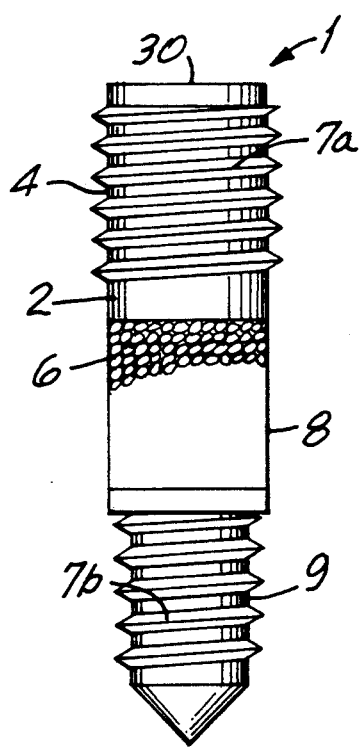
FIG. 3 is a side elevation view showing a modification of the screw shown in FIG. 2.

Referring again to the drawings, there are shown in FIGS. 2 and 3 further preferred embodiments of a threaded screw which incorporate a porous-coated portion constructed in accordance with the present invention. In the embodiment shown in FIG. 2, the screw includes a head portion 5 on one end of a cylindrical shaft 2. The head portion 5 has located immediately adjacent a threaded proximal region or section 4 of the shaft 2 which, in turn, is followed by an adjacent intermediate section 8. As shown in this embodiment, intermediate section 8 has a surface layer of porous bone ingrowth material 6 for permanent fixation of the screw to the bone. The intermediate section 8 is followed, in turn, by an adjacent, distal, region or section 9. As shown in this embodiment the proximal section 4 and the distal section 9 are both provided with screw threads 7a and 7b, respectively, for initial fixation of the screw, e.g., in the subchondral and inner cortical plates of the acetabulum or in the lateral and medial cortical plates of the acetabulum. The diameter of the thread 7a is larger than the outer diameter of porous section 8 while the diameter of the thread 7b is preferably equal to but may be smaller than the diameter of the porous section 8.

In use of the embodiment shown in FIG. 2 with present acetabular cups, the bone screws are installed in the manner discussed above for the FIG. 1 embodiment. However, in this embodiment the proximal section 4 and the distal section 9 of the shaft 2 are preferably designed to engage both the subchondial and inner cortical plates of the acetabulum for initial fixation of the screw and the acetabular prosthesis, and thus provide increased stability for the prosthesis during the bone formation period. During bone ingrowth, stresses originally carried by the threaded sections 4 and 9 of the screw are gradually shared by the porous-coated bone ingrowth section 8, resulting in a reduced stress load carried by the threaded sections 4 and 9. As a result, the impact of bone resorption in the area of the threaded sections 4 and 9 of the screw is minimized, since the porous-coated bone ingrowth section 8 continues to carry stresses throughout the life of the implant. As with the embodiment in FIG. 1, acetabular prosthesis stresses are also minimized, yielding more reliable and stable long-term fixation of prostheses to bone.

A further advantage of the present invention in connection with acetabular cups is that the resistance to shear stresses is dramatically increased throughout the life of the prosthesis, so long as bone ingrowth continues to occur. In addition, bone ingrowth into the porous-coated bone ingrowth section 8 of the shaft 2 will assist in preventing the acetabular prosthesis from sinking into the pelvis in direct relation to the shear resistance provided by trabecular bone that has successfully migrated into the porous-coated bone ingrowth section 8 of the screw.

The preferred embodiments of this invention are especially useful in addressing the surgical requirements of osteoporosis. For example, in the case of total hip arthroplasty, the acetabulum trabecular bone may become so diseased that it cannot adequately support a regular bone screw. To optimize initial fixation in such a situation, bicortical fixation screws are used to provide threaded engagement in both the lateral and medial cortical plates. Such circumstances provide a preferred situation for the embodiment depicted in FIG. 2. In this embodiment, the thread 7a of the proximal section 4 and thread 7b of the distal section 9 are capable of engaging both cortical bone plates for initial fixation, while the porous-coated bone ingrowth surface of the intermediate section 8 is situated to increase the long-term fixation of the screw and hence the prosthesis by receiving trabecular bone ingrowth.

As with FIG. 1, the embodiment shown in FIG. 2 utilizes a precisely drilled hole in the bone. Preferably, the porous-coated section 8 makes an interference or "scratch" fit with the sides of the borehole. Consequently, the crest of thread 7b of distal section 9 should not engage the sides of the borehole which will contact the porous material, and should have an outer or major thread diameter less than or equal to that of both the borehole and the porous-coated section 8.

The borehole preferably has a depth at least equal to the combined length of the proximal section 4 and porous-coated section 8. Distal section 9 may engage the sides of a smaller borehole drilled below an upper and larger borehole or may be inserted without a pilot hole. Both the proximal and distal threads 7a and 7b of sections 4 and 9 engage the boreholes by threading the screw into place, and the porous-coated section 8 preferably forms a tight interference fit with the surrounding preferably unthreaded sides of the borehole.

The embodiment shown in FIG. 3 is similar to the embodiment described with reference to FIG. 2, differing therefrom primarily in the elimination of the head 5. Instead, the driving end 30 of the shaft 2 is provided with any well known recessed tool receiving socket or means (not shown). In use, the threads 7a and 7b provide for initial fixation of the screw shaft 2 as it wedges between the bone plug of a bone-tendon autograft and the long walls of the femoral or tibial hole in an interference fit, as shown in FIGS. 6A and 6B.

The bone screw of FIG. 3 is installed in a manner similar to conventional interference screws. As discussed above, since bone formation around screws is active for approximately six to eight weeks, the threaded (proximal) section 4 and the threaded (distal) section 9 of the screw will provide increased stability for the prosthesis during this time. During this period of initial stability the porous-coated (intermediate) section 8 allows for bone ingrowth to ultimately provide long-term fixation of the screw and implant. With bone ingrowth, the porous-coated intermediate section 8 will continuously carry loads throughout the life of the bone-tendon graft, thereby reducing the transfer of stresses from the interference screw to the graft. The impact of bone resorption around the interference screw and bone-tendon graft is limited by the decreased transfer of stresses, resulting in a more reliable and stable long-term fixation.

The embodiment of the invention in FIG. 3 is preferably employed in addressing the surgical requirements of anterior cruciate ligament repair. For example, to assist in alleviating the long-term problem of bone-tendon autograft failure by eventual pull-out of the graft, the porous-coated section 8 provides continual and stable resistance due to the integration of the porous coating with both the bony surround and the bone plug of the autograft. The proximal and distal threaded sections 4 and 9 also provide increased resistance to outward forces due to decreased bone remodeling in the face of less stress transfers.

As with FIG. 2, the embodiment shown in FIG. 3 preferably utilizes an interference fit between the porous-coated section 8 and the sides of the bone plug 24, as shown in FIG. 6B. The outer diameter of the thread 7b of the distal section 9 should be no greater than the diameter of the porous-coated section 8, and preferably smaller, so as not to interfere with the formation of an interference fit between the section 8 and a portion of the bone plug 24, as shown in FIG. 6B.

Figure 4:
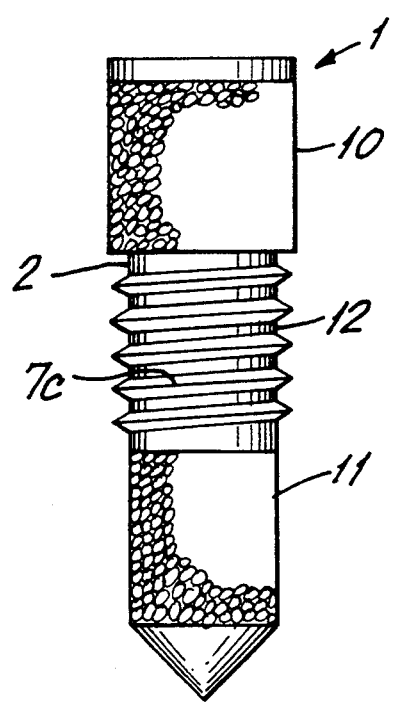
FIG. 4 is a side elevation view of another embodiment of the present invention.

A variation of the embodiments shown in FIGS. 2 and 3, is shown in FIG. 4, to which attention should now be directed. The bone screw illustrated therein has a threaded screw section 12 surrounded by proximal, 10, and distal, 11 porous-coated sections for long-term fixation. Initial fixation is provided by thread 7c on section 12. This embodiment provides for permanent fixation of the screw at both ends.

Unlike the prior embodiments shown in FIGS. 2 and 3, the embodiment shown in FIG. 4 has the two porous sections 10 and 11 of different diameters, a proximal larger diameter section 10 and a distal smaller diameter section 11. The bone screw of FIG. 4 is preferably installed using two borehole diameters, a smaller diameter to provide an interference fit with the distal porous section 11 and a larger diameter to provide an interference fit with the proximal porous section 10. Preferably, the smaller diameter borehole has a depth substantially equal to the length of shaft 2, and the larger diameter is provided as a counterbore only as deep as the length of proximal porous section 10. After insertion and threading of the bone screw into the borehole, the thread 7c of intermediate threaded section 12 engages the borehole sides only along the intermediate portion of the borehole since the larger proximal diameter has preferably already been bored. Upon threading completion, both porous sections 10 and 11 have preferably formed close interference fits with the surrounding bone.

The screws for all of the embodiments of the present invention are preferably made from any biocompatible material such as stainless steel, cobalt-chromium, titanium, their respective alloys, or composite materials.

The head portion 5 of the screws of the above embodiments is preferably provided with slots or other means on the driving end of the shaft 2 by which the screw shaft can be longitudinally rotated to enable the threads to engage the bone, e.g., by use of a screw driver. Any typical screw head type may be used in the present invention, including slotted for use with ordinary screw drivers, Phillips, hexagonal for use with an Allen wrench, torque or any other shape which can be manually or mechanically driven.

As shown in the drawings of the described embodiments, the head portion 5 of the screws may also vary in shape, depending upon the circumstances and intended use. The screw shown in FIG. 1 has a conventional flat head with a standard conical seat. A prosthetic device or other component using such screws preferably has a socket or countersink for receiving the screw head, thereby providing additional anchoring. The head shape shown in FIG. 2 has a spherical seat and preferably engages a spherical countersunk hole. The screws in FIGS. 3 and 4 have no head and are preferably used for interference fits. It is to be understood that additional screw head shapes and drive means for engaging the screw heads not shown are nonetheless within the scope of the claimed invention.

The porous-coated bone ingrowth material on the surface of the screws within the regions 3, 8, 10 and 11 may include spherical powders, fiber structures and plasma sprayed coatings in addition to any other biocompatible porous coating. The porous-coated materials may include materials such as Co-Cr-Mo, for F75 systems, or Ti-6A1-4V for F136 systems. The material can be gravity sintered, diffusion bonded or sprayed onto the surface of implant screws to form average pore sizes of about 350 microns. Gravity sintering typically involves heating the material to within 90–95% of its melting point. Diffusion bonding utilizes a combination of pressure and temperature typically reaching 50–60% of the melting point to create a bond between the ingrowth material and the material to be coated.

The screws of the present invention can also be made in a variety of sizes to provide for varying situations. Although standard diameters for the embodiments shown in FIGS. 1 and 2 are 6.5 mm and 4.5 mm in order to conform to standardized acetabular cup holes, and the standard diameter for the embodiments of FIGS. 3 and 4 is 9 mm, it is understood that these diameters can vary. The length of the screw and the respective longitudinal lengths of the porous-coated bone ingrowth surface sections and the threaded surface sections along the screw shaft can also vary. The preferred screw length ranges from 15–60 mm although the use of both shorter and longer screws are common. It is further understood that the porous-coated bone ingrowth and threaded sections need not be contiguous but may be separated from each other by varying amounts. Further, the sections are preferably separated along transverse lines perpendicular to the longitudinal or driving axis of the screw. Nonetheless, it should be understood that the shaft sections of the screw can be separated along non-perpendicular transverse lines which are preferably but not necessarily parallel to each other.

It should also be understood that the shaft of any of the embodiments of the present invention can include more than three alternating threaded and ingrowth sections along all or a portion of the shaft.

FIG. 5 depicts the attachment of an acetabular cup prosthesis to the pelvis through the use of bone screws according to the present invention. For this installation, a cup-shaped opening or socket 15 is reamed in the acetabulum region of the pelvis. Then, fixation boreholes are drilled into the bone to an appropriate depth, configuration and diameter corresponding to the length of the previously described screw that is to be installed. Next, a prosthetic acetabular cup 13, typically having a porous-coated convex surface 14, is inserted into the reamed socket 15. Acetabular cup 13 has at least one or more mounting holes 16. Screws according to the invention, such as those depicted in FIGS. 1 or 2, are inserted through the mounting holes 16 in the prosthetic acetabular cup 13, and into the boreholes drilled into the bone. Preferably, bone screws as shown in FIG. 2 are used to secure the prosthetic device. Preferably, the threaded proximal section 4 of the screw adjacent the screw head 5 engages subchondral plate bone 17, porous-coated screw section 8 contacts trabecular bone 18, and the threaded distal section 9 of the screw engages bone of the inner cortical plate 19, as shown in FIG. 5. The screws are preferably screwed into the cortical bone 19 of the pelvis through the boreholes until the head 5 of the screw engages a countersink or seats 20 of the prosthetic member 13, thereby affixing prosthetic cup 13 in acetabular socket 15. A plastic member 21 with a low friction concave surface 21a is then preferably placed over the prosthetic acetabular cup 13 and bone screws to provide a smooth surface in contact with the femoral head 22 of a femoral prosthesis 23, having a femoral stem 24 which is embedded within the femur.

FIG. 6 illustrates the use of screws of the present invention, such as that illustrated in FIG. 3, in the fixation of a bone plug for a bone-tendon autograft within a knee joint. It should be understood, however, that the screw described with reference to FIG. 4 could be used in the same manner. For this installation, a bone-tendon autograft is first secured from the knee and the appropriate femoral and tibial holes are drilled. The patellar and tibial bone plugs of the autograft are then placed within the femoral and tibial holes, respectively, such that the autograft bone plugs are in contact with the bony walls of the hole. As shown in FIG. 6A, patellar bone plug 24 fits inside a femoral borehole 25 in the femur 26. Patellar ligament 27 attaches the patellar bone plug 24 and the tibial bone plug (not shown). As shown in FIG. 6A, patellar bone plug 24 fits loosely within the femoral hole 25, leaving a clearance space 28 between the sides of femoral hole 25 and patellar bone plug 24.

FIG. 6B shows patellar bone plug 24 wedged against the side wall of femoral hole 25 after insertion of a bone screw 1 in accordance with the present invention, such as that shown in FIG. 3. Insertion of at least one bone screw into space 28 removes the clearance between the plug 24 and hole 25 and secures one end of the autograft via an interference fit. Screws of the present invention can also secure the tibial bone plug at the other end of the bone-tendon autograft.

Although specific embodiments of the invention have been described and illustrated, it is to be understood that modifications can be made without departing from the true spirit and scope of the invention as defined in the appended claims. For example, it should be apparent that the invention can be applied to prosthesis other than those in an artificial hip joint, the hip environment being used merely for purposes of illustration. Such examples include, inter alia, fracture plate fixation, and knee, elbow and shoulder replacements. It should be appreciated by those skilled in the art that the invention can be used in conjunction with any implant which requires attachment to bone.

It should also be understood that the screws shown in FIGS. 2 and 3 of the present invention can be used to engage a plurality of different bones, e.g., in bicortical or tricortical fixation, or they may engage a single cortical bone.

It should be understood, for example, that the embodiment of FIG. 4 can be provided with a head.

Although a tight fit is preferred for many uses, under certain circumstances the shafts of the screws of the present invention need not vary in diameter. For instance, threaded proximal sections 4 and 10 and distal sections 9 and 11 of the embodiments of FIGS. 2 to 4 may have substantially equal diameters. Thus, in threading the bone screw of FIG. 2 in a borehole having a length equal to the shaft 2 length, thread 7b of distal section 9 first engages the sides of the borehole. Upon further threading of the bone screw the thread 7a of proximal section 4 engage the sides of the borehole, preferably following the grooves formed by the distal thread 7b. The threads for both sections must have the same pitch and size and be oriented so that the proximal threads 7a tracks the grooves of the distal thread 7b.

Also, screws in accordance with FIG. 4 can have porous sections 10 and 11 of substantially equal diameter.

What is claimed is:

1. A bone screw comprising:
    a shaft of circular cross section having a driving end provided with a tool engaging means, and an opposite leading end;
    said shaft from said driving end to said leading end being divided into a plurality of adjacent coaxially aligned longitudinal regions, at least two of said regions that are not contiguous having an external bone ingrowth porous circumferentially continuous surface free from threads along their respective lengths, and at least one of said regions located between said two porous surface regions having an externally threaded non-porous surface throughout its length.

2. A bone screw as claimed in claim 1, having a circular head portion integral with said driving end of said shaft, said head portion having a larger diameter than the outer diameter of said region on said shaft closest to said head portion, and wherein said head portion includes said tool engaging means.

3. A bone screw as claimed in claim 1, wherein said two porous surface regions have different diameters with the region of larger diameter being located nearer said driving end of the shaft than the region of smaller diameter, and said region with a threaded surface has a smaller crest diameter than said larger diameter porous surface region.

4. A bone screw as claimed in claim 1, wherein said porous surface region that is nearer said leading end of said shaft has a smaller diameter than the crest diameter of said threaded surface region.

5. A bone screw as claimed in claim 1, composed of a biocompatible material.

6. A bone screw as claimed in claim 1, composed of a material selected from the group consisting of stainless steel, cobalt-chromium, titanium, alloys thereof, and composite materials.

7. A bone screw as claimed in claim 1, wherein said bone ingrowth porous surface is provided by a material selected from the group consisting of spherical powders, fiber structures, and plasma-sprayed coatings.

* * * * *